United States Patent
Cantlon

(10) Patent No.: US 8,489,208 B2
(45) Date of Patent: Jul. 16, 2013

(54) KEY LOCKING ANCHORING DEVICE FOR IMPLANTED LEAD

(75) Inventor: Kurt Cantlon, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 225 days.

(21) Appl. No.: 12/878,483

(22) Filed: Sep. 9, 2010

(65) Prior Publication Data

US 2011/0060395 A1    Mar. 10, 2011

Related U.S. Application Data

(60) Provisional application No. 61/240,942, filed on Sep. 9, 2009.

(51) Int. Cl.
*A61N 1/372*    (2006.01)

(52) U.S. Cl.
USPC ............ 607/149; 607/116; 607/126; 606/232

(58) Field of Classification Search
None
See application file for complete search history.

(56) References Cited

U.S. PATENT DOCUMENTS

| | | | | |
|---|---|---|---|---|
| 4,672,979 A | * | 6/1987 | Pohndorf | 607/126 |
| 5,107,856 A | * | 4/1992 | Kristiansen et al. | 607/126 |
| 5,152,298 A | * | 10/1992 | Kreyenhagen et al. | 607/116 |
| 5,242,431 A | * | 9/1993 | Kristiansen | 604/533 |
| 5,843,146 A | * | 12/1998 | Cross, Jr. | 607/115 |
| 5,957,968 A | * | 9/1999 | Belden et al. | 607/126 |
| 6,473,654 B1 | * | 10/2002 | Chinn | 607/126 |
| 7,591,970 B2 | | 9/2009 | Olson | |
| 7,787,960 B2 | * | 8/2010 | Lubenow et al. | 607/116 |
| 7,930,039 B2 | * | 4/2011 | Olson | 607/126 |
| 2007/0078399 A1 | | 4/2007 | Olson | |
| 2009/0312712 A1 | | 12/2009 | Olson | |

OTHER PUBLICATIONS

U.S. Appl. No. 12/502,068, filed Jul. 13, 2009.

* cited by examiner

*Primary Examiner* — Kennedy Schaetzle

(57)    ABSTRACT

There is disclosed various embodiments of an implantable anchor for anchoring a medical lead within a patient. The implantable anchor includes a body having a cavity for receiving a medical lead, and a separate, removable key for insertion into the cavity. The key, upon insertion into the cavity, engages and locks the medical lead into place and prevents the movement of the medical lead with respect to the anchor.

11 Claims, 5 Drawing Sheets

KEY LOCKING ANCHORING DEVICE FOR IMPLANTED LEAD

CROSS-REFERENCE TO RELATED APPLICATIONS

This application claims the benefit of U.S. Provisional Application No. 61/240,942, filed Sep. 9, 2009, which is incorporated herein by reference.

TECHNICAL FIELD

The present application is generally related to an implantable anchor for anchoring an electrical stimulation lead, a drug infusion catheter, or other catheter of an implantable medical device system.

BACKGROUND

A number of implantable medical devices have been commercially distributed that allow various medical agents to be controllably infused after implantation of the respective device within a patient. For example, implantable medical devices are used for the infusion of insulin, opiates, antispasmodic drugs, intrahepatic chemotherapy agents, and other therapeutic agents in a number of countries subject to the regulatory requirements of those countries.

There are a number of benefits to the use of implantable infusion devices. For example, when the therapeutic agent is delivered directly to the therapy site (for opiates and baclofen), the amount of the therapeutic agent that is needed is much lower. Side-effects are generally minimized. Also, the therapeutic effect can be significantly greater as compared to intravenous introduction of therapeutic agents (again, for opiates and baclofen). Furthermore, implantable infusion devices eliminate patient overdosing or underdosing due to patient error or limited patient capacity.

Implantable infusion devices typically include a central housing that includes a reservoir to hold the infusate, a septum to allow infusate to be introduced into the reservoir, an energy source to drive the infusate from the reservoir and through an outlet port, and various flow control elements. The central housing portion of the device is typically implanted in a suitable subcutaneous region with the septum positioned immediately below the skin of the patient to facilitate access to the reservoir for refilling purposes.

To deliver the infusate from the reservoir, a catheter is usually attached to the outlet port of the central housing to receive the infusate outflow. The distal end of the catheter is implanted within the patient adjacent to the appropriate therapy site (e.g., at a suitable intrathecal location to allow introduction of an infusate directly into the spinal fluid of the patient). Typically, some mechanism is employed to anchor the catheter so that infusate will continue to be delivered to the appropriate site such as sutures and/or anchoring structures.

Anchoring is also used in spinal cord stimulation (SCS) systems. In SCS systems, a pulse generator is typically implanted within a subcutaneous pocket within the patient. An electrical lead is also implanted within the patient. The proximal end of the electrical lead is electrically coupled (either directly or via one or more extensions) to the pulse generator to receive electrical pulses from the pulse generator. The distal end of the electrical lead is positioned with electrodes of the lead disposed within the epidural space of the patient to deliver the electrical pulses to the spinal neural tissue of the patient. The efficacy of the electrical stimulation in treating chronic pain of the patient depends upon applying the electrical pulses to the appropriate neural tissue. Accordingly, it is desired to retain the stimulation lead at a relatively fixed position over time. For that reason, the electrical lead is anchored so that migration of the electrical lead does not occur.

SUMMARY

In one embodiment, there is disclosed various embodiments of an implantable anchor for anchoring a medical lead. In one embodiment, the implantable anchor may include a base and corresponding key, both being configured, such that when assembled together, create a torturous path for the medical lead. The base is configured to receive the medical lead and the key, such that when the key is inserted into the base, a mechanical lock is created between the key, the lead and the base, thereby restricting the migration of the lead placement within a body, as well as restricting the ejection of the lead from the pulse generator.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
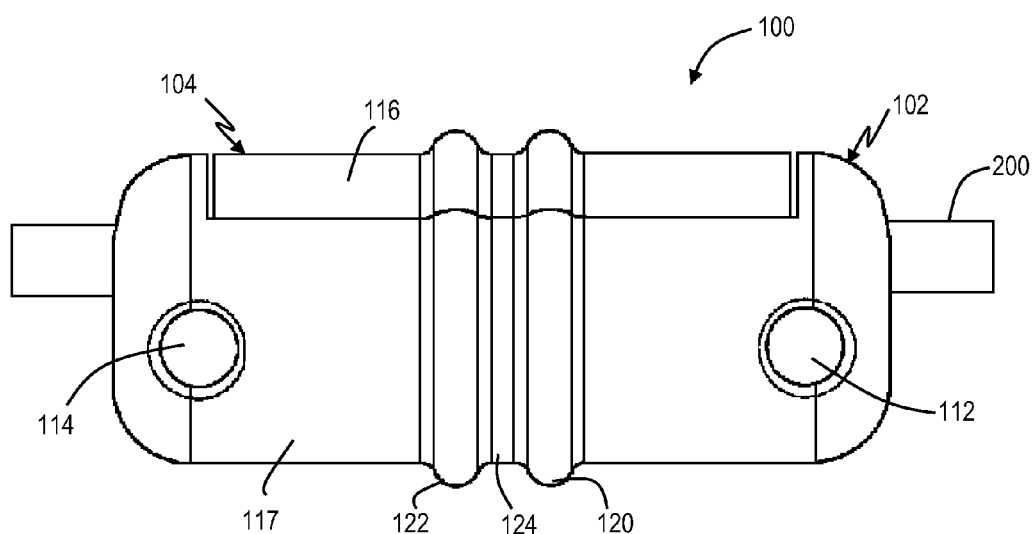
FIG. 1 is a side view illustrating one embodiment of an implantable anchor.

For the purposes of promoting an understanding of the principles of the present invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

Figure 2:
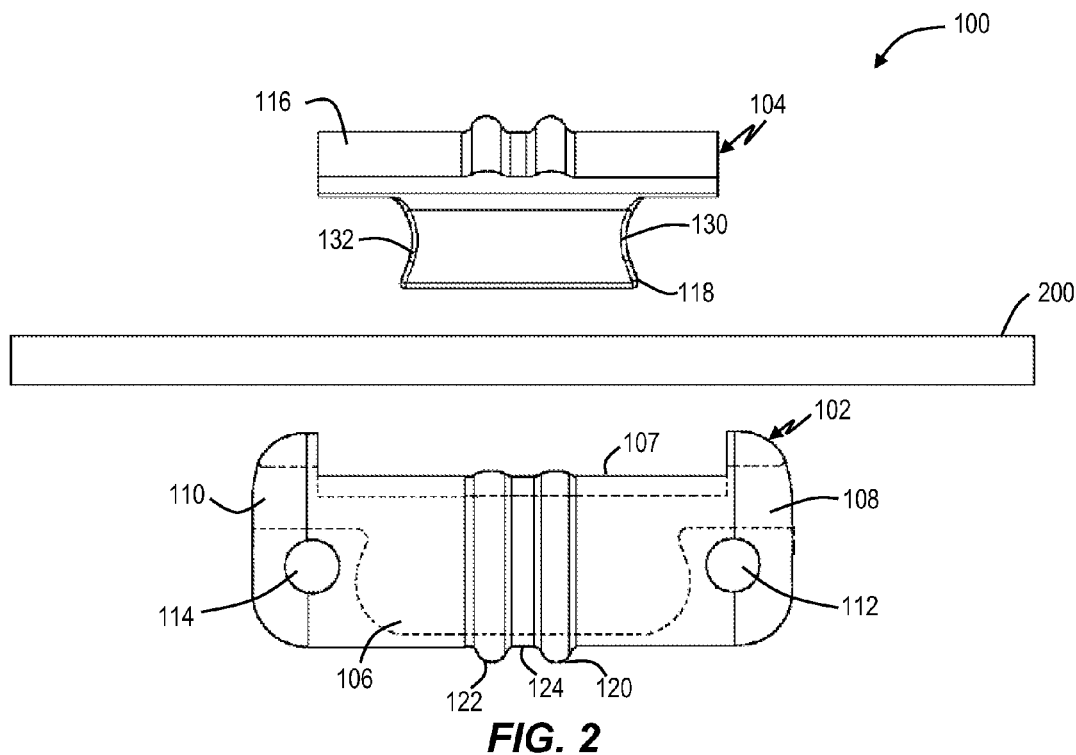
FIG. 2 is an exploded side view illustrating an embodiment of an implantable anchor as similarly shown in FIG. 1.
Figure 3:
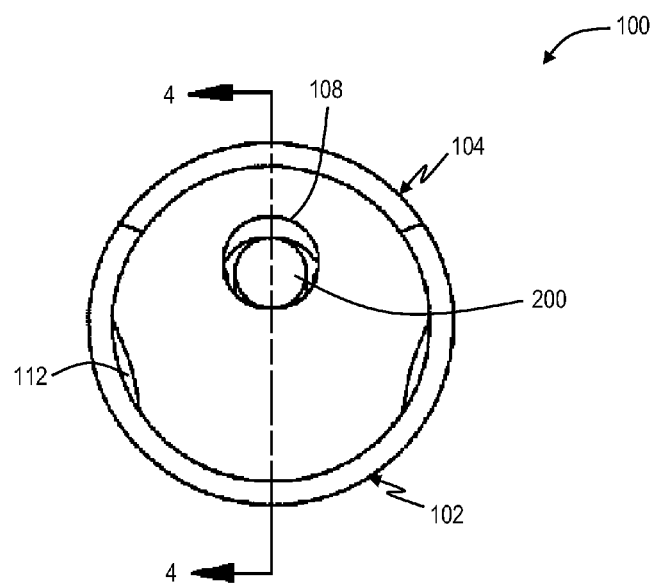
FIG. 3 is an end view of an embodiment of an implantable anchor as similarly shown in FIG. 1.
Figure 4:
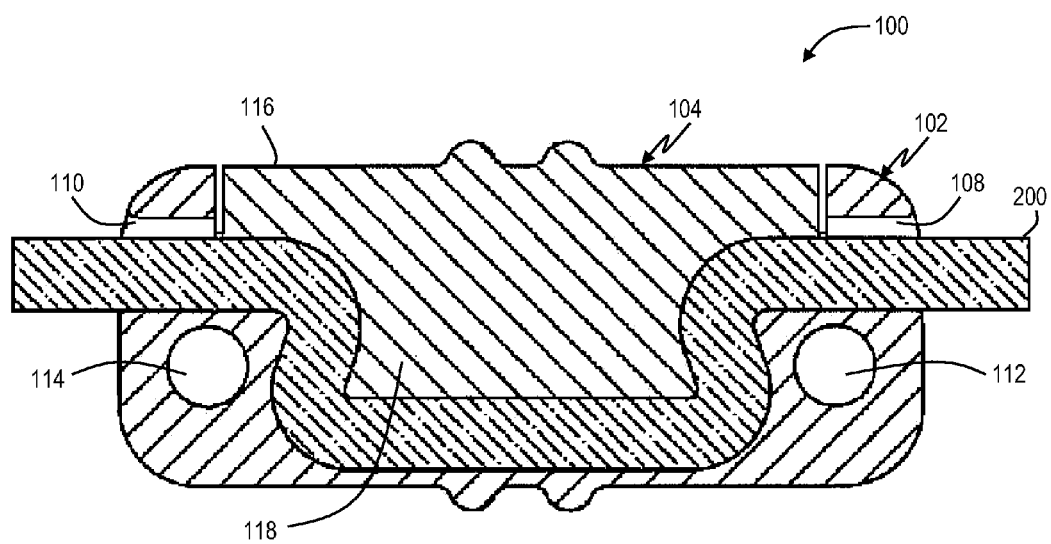
FIG. 4 is a cross-sectional view of an embodiment of an implantable anchor as taken along line 4-4 of FIG. 3.

FIGS. 1 through 4 depict an implantable anchor 100, with FIG. 2 illustrating the anchor 100 in a first or unlocked configuration, and FIGS. 1, 3 and 4 illustrating the anchor 100 in a second or locked configuration. The anchor 100 may be used for anchoring a drug infusion catheter, an electrical lead, or other catheter (not shown) according to one representative embodiment. For the purpose of this disclosure, the term "lead" is used in a broad manner and should be interpreted to encompass both infusion catheters and stimulation leads.

Anchor 100 includes a base 102 and a key 104. Base 102 includes a cavity 106 which is configured to receive a lead 200 therein (see FIG. 4). Base 102 includes an opening 107 for receiving key 104 into cavity 107. Positioned at opposite ends of base 102 are openings 108 and 110, with openings 108 and 110 being sized to facilitate the reception of lead 200 therethrough. Base 102 also includes suture holes 112 and 114 which extend through base 102.

Key 104 includes an outer portion 116 and an inner portion 118. Inner portion 118 is shaped and configured to be inserted into cavity 106 of base 102, and when inserted, engages and locks lead 200 into base 102. The curved portions 130 and 132 of key 104 and the shape of cavity 106 are configured such that when lead 200 is positioned between key 104 and base 102 (see FIG. 4) a mechanical lock is created inhibiting the removal of key 104 from base 102 and inhibiting the migration of lead 200 with respect to anchor 100.

Integrated with the external surface 117 of base 102 and the external surface 116 of key 104 are ribs 120 and 122. Ribs 120 and 122 are configured, such that when key 104 is inserted into base 102, the ribs 120 and 122 circumscribe anchor 100, creating a groove 124 therebetween. Ribs 120 and 122 and grove 124 facilitate the suturing of anchor 100 to tissue of the patient, as well as securing key 104 within base 102.

In certain embodiments, the anchor 100 may be fabricated using any suitable polymer processing technique. The polymer or polymers selected for the anchor 100 are preferably adapted for long term implantation. Biocompatibility and biostability are characteristics for the polymer selection for anchor 100. Also, the polymer preferably possesses a medium to high durometer to maintain the structural characteristics of anchor 100. An example of a suitable polymer for anchor 100 is polyetheretherketone (PEEK), although any biostable, biocompatible polymer having a suitable durometer and a suitable coefficient of friction can be employed.

In use, anchor 100 is placed in the unlocked position (see FIG. 2) with key 104 being removed from base 102. Base 102 is placed on the proximal end of lead 200 with lead 200 extending through openings 108 and 110. Base 102 is slid over the lead 200 until the anchor 100 is properly positioned along the lead 200. Key 104 is then inserted into cavity 106 of base 102, and engages lead 200. Key 104 forces lead 200 along the bottom of cavity 106 (see FIG. 4) creating a torturous path for lead 200 through anchor 100 and mechanically locks key 104 within cavity 106, thereby inhibiting the migration of lead 200 with respect to anchor 100.

Channel 124 and suture holes 112 and 114 are used to facilitate the suturing of anchor 100 to tissue of the patient, while channel 124 further facilitates securing key 104 within base 106.

The diameters of openings 108 and 110 and size of cavity 106 are sufficiently large to permit the introduction of lead 200 with little difficulty. Thus, when the key 104 is removed from base 102, the anchor 100 may be freely moved along the lead. However, when the key 104 is inserted into cavity 106 of base 102, the internal portion 118 of key 104 extends into cavity 106, engaging lead 200 and creating a compressive force to cause anchor 100 to hold the lead 200 in place and lock key 104 within base 102. The lead 200, therefore, is inhibited from slipping through the anchor 100.

Figure 6:
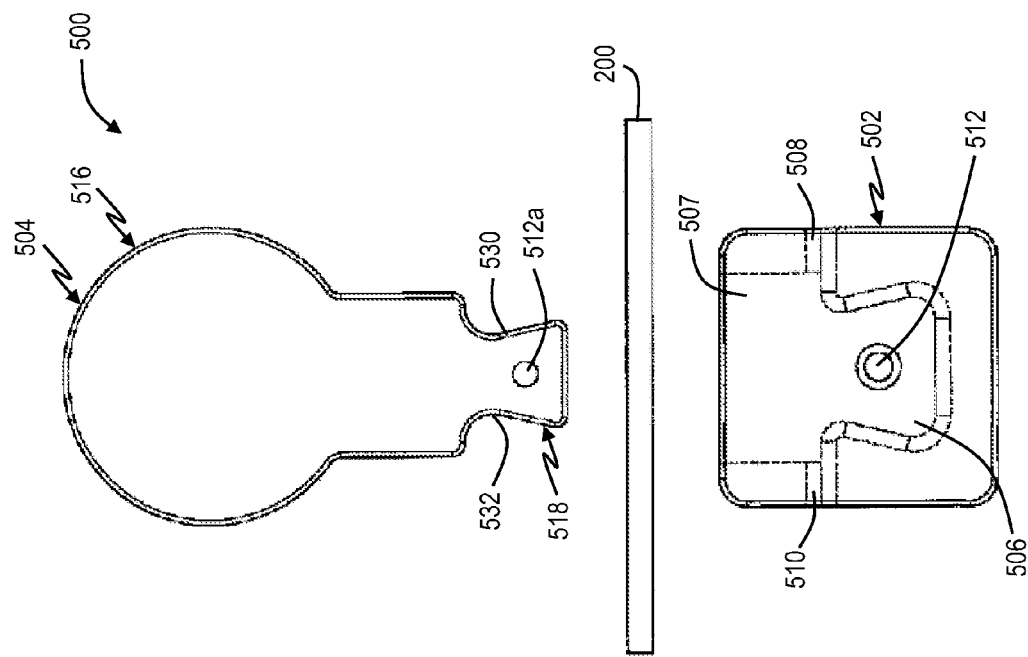
FIG. 6 is an exploded side view illustrating an embodiment of an implantable anchor as similarly shown in FIG. 5.
Figure 5:
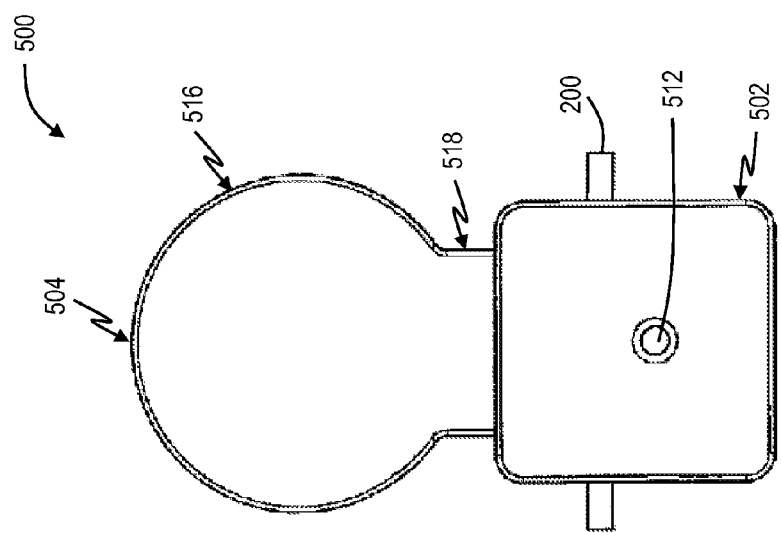
FIG. 5 is a side view illustrating another embodiment of an implantable anchor.
Figure 8:
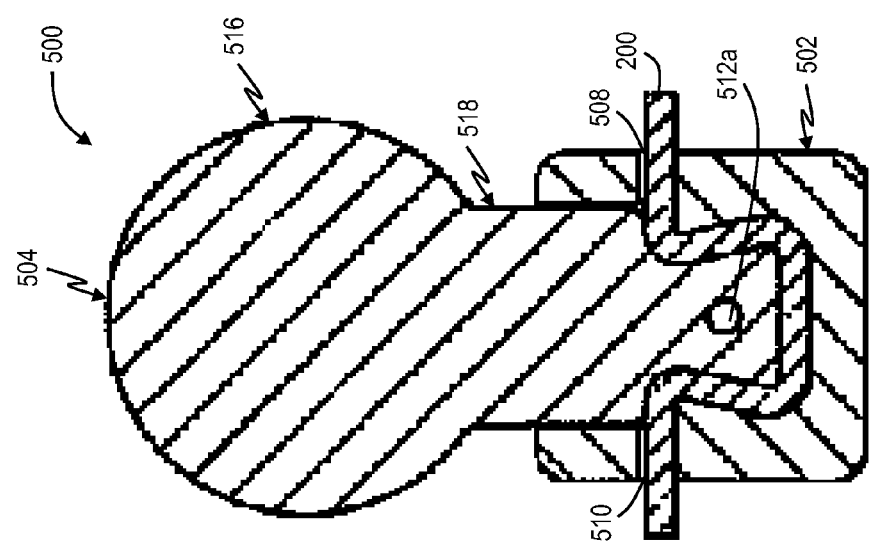
FIG. 8 is a cross-sectional view of an embodiment of an implantable anchor as taken along line 8-8 of FIG. 7.
Figure 7:
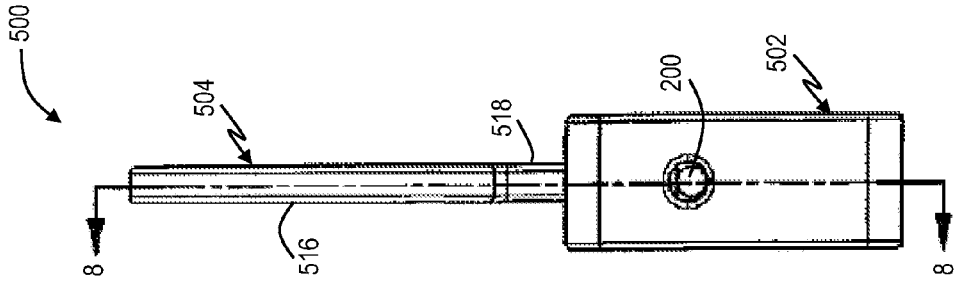
FIG. 7 is an end view of an embodiment of an implantable anchor as similarly shown in FIG. 5.

FIGS. 5 through 8 depict an implantable anchor 500, with FIG. 6 illustrating the anchor 500 in a first or unlocked configuration, and FIGS. 5, 7 and 8 illustrating the anchor 500 in a second or locked configuration. The anchor 500 may be used for anchoring a drug infusion catheter, an electrical lead, or other catheter (not shown) according to one representative embodiment. As with the anchor described herein above with respect to FIGS. 1-4, the term "lead" is used in a broad manner and should be interpreted to encompass both infusion catheters and stimulation leads.

Anchor 500 includes a base 502 and a key 504, with each of base 502 and key 504 being generally planar and of low profile. Base 502 includes a cavity 506 which is configured to receive a lead 200 therein (see FIG. 8). Base 502 includes an opening 507 for receiving key 504 into cavity 507. Positioned at opposite edges of base 502 are openings 508 and 510, with openings 508 and 510 being sized to facilitate the reception of lead 200 therethrough. Base 502 also includes suture hole 512, while key 504 includes a corresponding suture hole 512a, which when aligned, through anchor 500.

Key 504 includes an upper portion 516 and a lower portion 518. Lower portion 518 is shaped and configured to be, at least partially, inserted into cavity 506 of base 502, and when inserted, engages and locks lead 200 into base 502. The curved portions 530 and 532 of key 504 and the shape of cavity 506 are configured such that when lead 200 is positioned between key 504 and base 502 (see FIG. 8) a mechanical lock is created inhibiting the removal of key 504 from base 502 and inhibiting the migration of lead 200 with respect to anchor 500.

In certain embodiments, the anchor 500 may be fabricated using any suitable polymer processing technique. The polymer or polymers selected for the anchor 500 are preferably adapted for long term implantation. Biocompatibility and biostability are characteristics for the polymer selection for anchor 500. Also, the polymer preferably possesses a medium to high durometer to maintain the structural characteristics of anchor 500. An example of a suitable polymer for anchor 500 is polyetheretherketone (PEEK), although any biostable, biocompatible polymer having a suitable durometer and a suitable coefficient of friction can be employed.

In use, anchor 500 is placed in the unlocked position (see FIG. 6) with key 504 being removed from base 502. Base 502 is placed on the proximal end of lead 200 with lead 200 extending through openings 508 and 510. Base 502 is slid over the lead 200 until the anchor 500 is properly positioned along the lead 200. Key 504 is then inserted into cavity 506 of base 502, and engages lead 200. Key 504 forces lead 200 along the bottom of cavity 506 (see FIG. 8) creating a torturous path for lead 200 through anchor 500 and mechanically locks key 504 within cavity 506, thereby inhibiting the migration of lead 200 with respect to anchor 500.

Suture hole 512 of base 502 and suture hole 512a of key 504, when aligned are operable to receive sutures which are used to facilitate the suturing of anchor 500 to tissue of the patient, and further used to facilitate additional securing key 504 within base 506.

The diameters of openings 508 and 510 and size of cavity 506 are sufficiently large to permit the introduction of lead 200 with little difficulty. Thus, when the key 504 is removed from base 502, the anchor 500 may be freely moved along the lead. However, when the key 504 is inserted into cavity 506 of base 502, the lower portion 518 of key 504 extends into cavity 506, engaging lead 200 and creating a compressive force to cause anchor 500 to hold the lead 200 in place and lock key 504 within base 502. The lead 200, therefore, is inhibited from slipping through the anchor 500.

Figure 9:
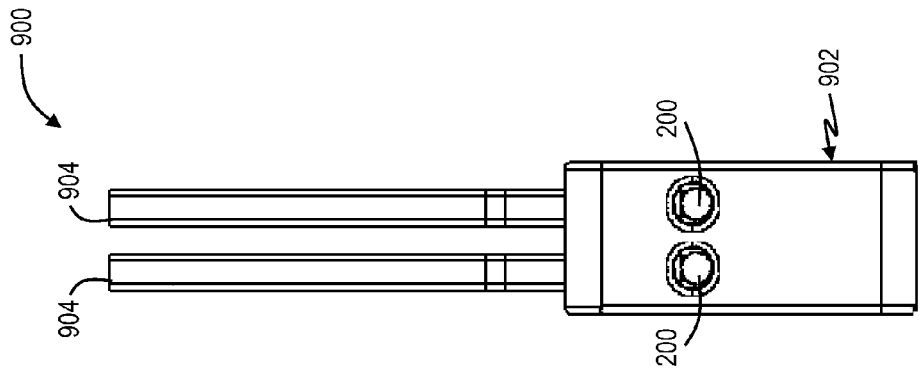
FIG. 9 is an end view of an alternative embodiment of an implantable anchor utilizing two keys and two leads.

Referring now to FIG. 9, there is illustrated an implantable anchor 900 configured to receive 2 separate leads 200 and locked with separate keys 904. As similarly described herein above with respect to FIGS. 5-8, base 902 if of sufficient thickness to include 2 cavities (such as cavity 506, FIG. 6), with each cavity being configured to receive leads 200 extending therethrough. A separate key 904 is inserted into each of the cavities to engage and lock leads 200 into place. Each of the keys 904 engage with their corresponding cavities as similarly described herein with respect to FIGS. 5-8.

Figure 10:
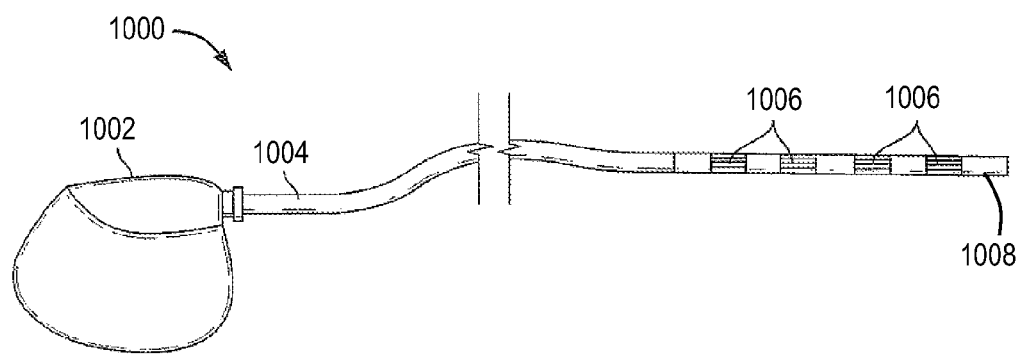
FIG. 10 depicts a conventional neurostimulation system that may utilize an anchor according to at least one representative embodiment.

Anchors according to representative embodiments may be utilized in conjunction with any suitable implantable medical device that comprises an implantable lead. For example, anchors 100, 500 and 900 can be utilized to anchor a stimulation lead of a neurostimulation system as shown in FIG. 10. A neurostimulation system 1000 includes a pulse generator 1002 and one or more stimulation leads 1004. An example of a commercially available pulse generator is the EON® product available from St. Jude Medical, Inc. An example of a commercially available stimulation lead is the Axxess® lead available from St. Jude Medical, Inc.

The pulse generator 1002 is typically implemented using a metallic housing that encloses circuitry for generating the electrical pulses for application to neural tissue of the patient. The pulse generator 1002 is usually implanted within a subcutaneous pocket created under the skin by a physician. The lead 1004 is used to conduct the electrical pulses from the implant site of the pulse generator for application to the targeted nerve tissue via electrodes 1006. The lead 1004 typically includes a lead body of an insulative polymer material with embedded wire conductors extending through the lead body. The electrodes 1006 of the lead body are coupled to the conductors to deliver the electrical pulses to the nerve tissue. For example, the distal end 1008 of lead 1004 may be positioned within the epidural space of the patient to deliver electrical stimulation to spinal nerves to treat chronic pain of the patient. The anchors disclosed herein may be utilized to ensure that the distal end 1008 of the lead 1004 remains adjacent to the appropriate nerves associated with the chronic pain of the patient. In some embodiments, an "extension" lead (not shown) may be utilized as an intermediate connector if deemed appropriate by the physician.

In certain embodiments for SCS applications, the lead 1004 is a "body compliant" lead that possesses mechanical characteristics that allow the lead 1004 to stretch in response to forces experienced with the patient's body. For example, the lead 1004 may be adapted to stretch up to 25% in response to low stretching forces such as 2 pounds of force. The ability to exhibit significant elongation in response to such low forces enables the lead to be relatively robust (e.g., does not experience significant conductor breakage). Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference for all purposes.

Figure 11:
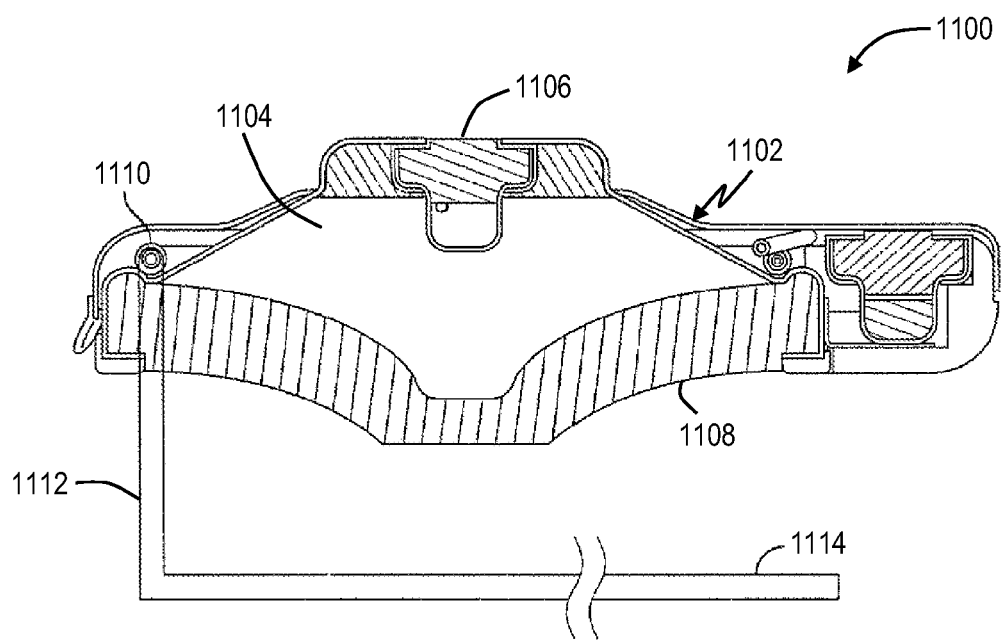
FIG. 11 depicts a conventional drug pump system that may utilize an anchor according to at least one representative embodiment.

Alternatively, the anchors 100, 500 and 900 can be utilized to anchor an infusion catheter of an implantable drug infusion device 1100 as shown in FIG. 11. The implantable infusion drug pump device 1100 may include a central housing 1102, a reservoir 1104 to hold the infusate, a septum 1106 to allow infusate to be introduced into the reservoir, an energy source 1108 (e.g., a spring diaphragm) to drive the infusate from the reservoir and through an outlet port 1110, and various flow control elements (not shown).

The central housing 1102 of the device is often implanted in a suitable subcutaneous region with the septum 1106 positioned immediately below the skin of the patient to facilitate access to the reservoir 1104 for refilling purposes. A catheter 1112 is attached to the outlet port 1110 of the central housing 1102 to receive the infusate outflow. A distal end 1114 of the catheter is implanted within the patient adjacent to the appropriate therapy site. The anchors 100, 500 and 900 may be utilized to ensure that the distal end 1114 of the lead 1112 remains adjacent to the appropriate site generating the chronic pain of the patient.

Although some representative embodiments have been discussed in terms of anchoring intrathecal and epidural catheters and leads, anchors can be employed according to alternative embodiments for any suitable location. For example, an anchor according to some embodiments could be used for peripheral nerve stimulation and gastric pacing applications.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

Any combination of the features discussed above are within the scope of certain embodiments of the present invention. Thus, a feature disclosed in reference to one embodiment may be combined with another embodiment. Furthermore, combinations of disclosed features and alternative features are within the scope of certain embodiments of the present invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. An implantable anchor for anchoring a medical lead within a user, the anchor comprising:
    an elongated base having a first end, a second end, a top, a bottom and a cavity, the cavity having an upper portion and a lower portion with the upper portion extending along a longitudinal axis from the first end to the second end, with each of the first end of the base and the second end of the base having an opening for receiving the medical lead, the base further having an opening extending from the top of the base into the upper portion of the cavity, the cavity for receiving the medical lead;

a key having a first elongated portion for insertion into the cavity of the base through the opening extending from the toy into the upper portion of the cavity, the first portion having a shape to mate with at least a portion of the cavity of the base;

wherein when the medical lead is disposed in the upper portion of the cavity of the base through the first end of the base to the second end of the base and when the first portion of the key is subsequently inserted into the cavity of the base with the elongated portion of the key being in parallel alignment with the longitudinal axis of the base, the key engages at least a portion of the lead forcing a portion of the lead into the lower portion of the cavity of the base creating a tortuous path for the lead through the base and thereby inhibiting the movement of the medical lead with respect to the anchor.

2. The implantable anchor of claim 1, further including a first suture hole extending through the base, the first suture hole to facilitate the suturing of the anchor to the user.

3. The implantable anchor of claim 1, wherein the cavity is configured to receive a second medical lead, the anchor further including a second key, the second key having a first portion for insertion into the cavity of the base, the first portion of the second key having a shape to mate with at least a portion of the cavity of the base, wherein when the second medical lead is disposed in the cavity of the base and the first portion of the second key is subsequently inserted into the cavity of the base, the key engages at least a portion of the second medical lead forcing a portion of the second medical lead into the lower portion of the cavity of the base creating a tortuous path for the second medical lead through the base and thereby inhibiting the movement of the second medical lead with respect to the anchor.

4. An implantable anchor for anchoring a medical lead within a living organism, the anchor comprising:

an elongated base having a cavity, the cavity for receiving the medical lead, the base having a top, a first end, a second end, the cavity having an upper portion and a lower portion with the upper portion extending along a longitudinal axis from the first end to the second end, with each of the first end of the base and the second end of the base having an opening for receiving the medical lead, the base further having an opening extending from the top of the base into the upper portion of the cavity, the base further including a first hole extending perpendicular to the longitudinal axis through the base;

a first key having an elongated portion for insertion into the cavity of the base, the first key having a second hole, the second hole extending through the first key;

wherein when the medical lead is disposed in the upper portion of the cavity of the base and the elongated portion of the first key is subsequently inserted into the cavity of the base in parallel alignment with the longitudinal axis of the base, the first key engages at least a portion of the medical lead and forces a portion of the medical lead into the lower portion of the cavity creating a tortuous path of the lead through the base and thereby inhibits the movement of the medical lead with respect to the anchor, and further wherein upon insertion of the elongated portion of the key into the cavity of the base, the first hole of the base and the second hole of the key align to receive a suture therethrough to secure the anchor to the living organism and to further secure the key within the cavity of the base.

5. The implantable anchor of claim 4, wherein each of the key and the base include a groove, such that when the key is inserted into the cavity of the base, the groove of the key is in alignment with the groove of the base, the groove of the base and the key to receive a suture for securing the key to the base.

6. The implantable anchor of claim 5, wherein the cavity is configured to receive a second medical lead, the anchor further including a second key, the second key having a portion for insertion into the cavity of the base, wherein when the second medical lead is disposed in the cavity of the base and the second key is subsequently inserted into the cavity of the base, the second key engages at least a portion of the second medical lead creating a tortuous path for the second medical lead and thereby inhibits the movement of the second medical lead with respect to the anchor.

7. An implantable anchor for anchoring a medical lead within a living organism, the anchor comprising:

a base having a top, a first end and a second end and further having a cavity, the cavity having an upper portion and a lower portion, the cavity for receiving the medical lead;

a first separate key having a portion for insertion into the cavity of the base;

the base further including an opening at the top for receiving the first key, the base including an opening at each of the first end and the second end, with the openings at the first and second ends configured to facilitate the passing of the medical lead therethrough;

wherein the medical lead passes through the openings at the first and second ends and is disposed in the upper portion of the cavity of the base, when the portion of the first key is subsequently inserted into the cavity of the base, the first key engages at least a portion of the medical lead and forces a portion of the medical lead into the lower portion of the cavity creating a tortuous path of the lead through the base and thereby inhibits the movement of the medical lead with respect to the anchor, and further wherein each of the key and the base include a groove, such that when the key is inserted into the cavity of the base, the groove of the key is in alignment with the groove of the base, the groove of the base and the key to receive a suture for securing the key to the base.

8. The implantable anchor of claim 7, further including a first hole extending through the base, the first hole to facilitate the suturing of the anchor to the user.

9. The implantable anchor of claim 8, further including a second hole extending through the key, such that when the medical lead is disposed in the cavity of the base and the key is inserted into the cavity of the base, the first hole and the second hole align to receive a suture therethrough to secure the anchor to the living organism and to further secure the key within the cavity of the base.

10. The implantable anchor of claim 9, wherein each of the key and the base include a groove, such that when the key is inserted into the cavity of the base, the groove of the key is in alignment with the groove of the base, the groove of the base and the key to receive a suture for securing the key to the base.

11. The implantable anchor of claim 10, wherein the cavity is configured to receive a second medical lead, the anchor further including a second key, the second key having a portion for insertion into the cavity of the base, wherein when the second medical lead is disposed in the cavity of the base and the second key is subsequently inserted into the cavity of the base, the second key engages at least a portion of the second medical lead and inhibits the movement of the second medical lead with respect to the anchor.

* * * * *